US006591984B2

(12) United States Patent
Odierno et al.

(10) Patent No.: US 6,591,984 B2
(45) Date of Patent: *Jul. 15, 2003

(54) NEEDLE SHEATHING AND UNSHEATHING SAFETY DEVICE

(76) Inventors: David Odierno, 104 Falcon St., East Boston, MA (US) 02128; Mike Hoftman, 22205 Dardenne Ave., Calabasas, CA (US) 91302

( * ) Notice: Subject to any disclaimer, the term of this patent is extended or adjusted under 35 U.S.C. 154(b) by 0 days.

This patent is subject to a terminal disclaimer.

(21) Appl. No.: 09/899,361

(22) Filed: Jul. 3, 2001

(65) Prior Publication Data

US 2001/0035362 A1 Nov. 1, 2001

Related U.S. Application Data

(63) Continuation-in-part of application No. 09/453,737, filed on Dec. 2, 1999, now Pat. No. 6,257,408.

(51) Int. Cl.⁷ .............................. B65D 83/10; B65D 6/04
(52) U.S. Cl. ........................ 206/366; 206/365; 206/563
(58) Field of Search ................................. 206/363–366, 206/370, 485, 562–564; 211/60.1, 85.13; 604/192, 263

(56) References Cited

U.S. PATENT DOCUMENTS

| | | | | |
|---|---|---|---|---|
| 2,659,485 A | * | 11/1953 | Duley et al. | 206/365 |
| 3,727,749 A | * | 4/1973 | Martin | 206/366 |
| 4,383,615 A | | 5/1983 | Aquino | |
| 4,658,957 A | * | 4/1987 | Guth et al. | 206/365 |
| 4,846,803 A | | 7/1989 | Emerson | |
| 5,090,564 A | * | 2/1992 | Chimienti | 206/365 |
| 5,279,578 A | * | 1/1994 | Cooke | 206/365 |
| 5,311,985 A | | 5/1994 | Suiza | |
| 5,469,964 A | | 11/1995 | Bailey | |

* cited by examiner

Primary Examiner—Luan K. Bui

(57) ABSTRACT

The present invention is a device where a needle cap rim is captured between a front wall and abutment means behind it. This is done by making aligned slots in the front wall and abutment means with side to side widths greater than the diameter of the needle cap body (without ridges) but less than the outside diameter of the needle cap rim. However, the rim of the needle hub is located outside the front wall slot, where the intervening needle hub rim to needle shaft part of the needle hub passes through the front wall slot and into the needle cap for friction fit contact.

13 Claims, 7 Drawing Sheets

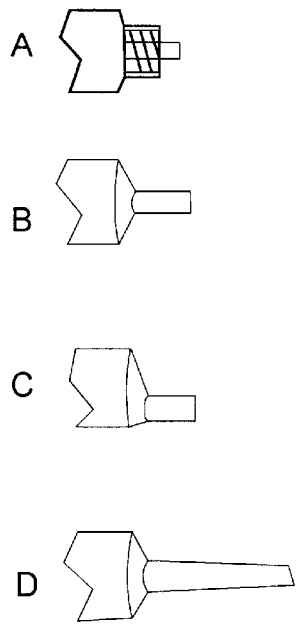
FIGURE 8
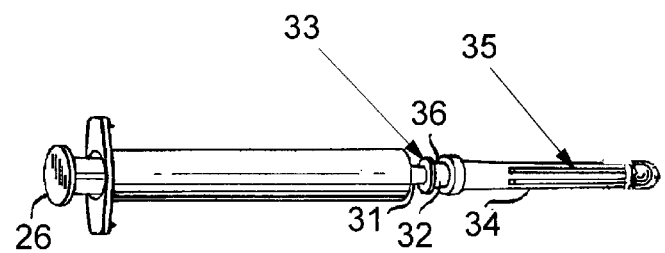
FIGURE 9
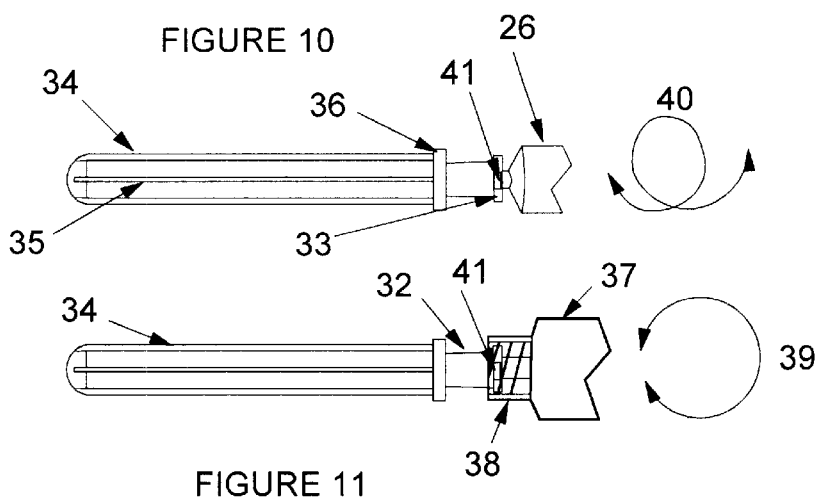

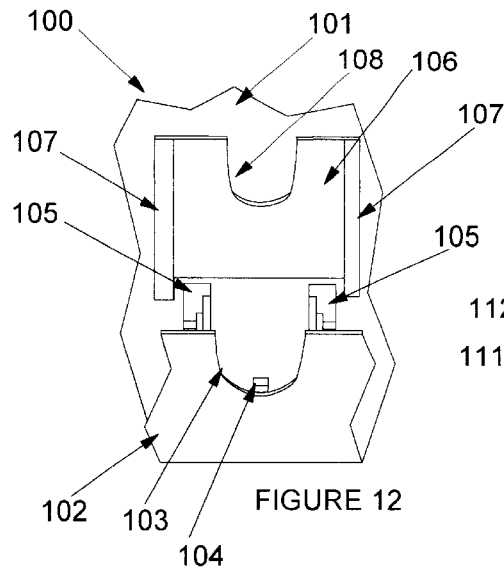
FIGURE 12
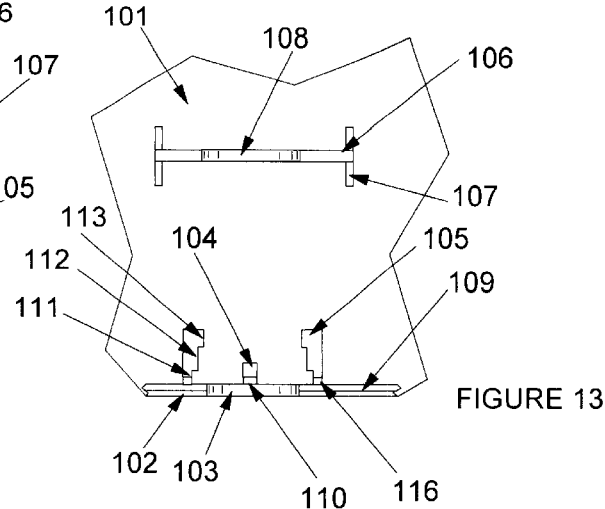
FIGURE 13
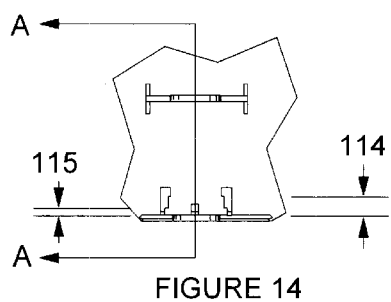
FIGURE 14
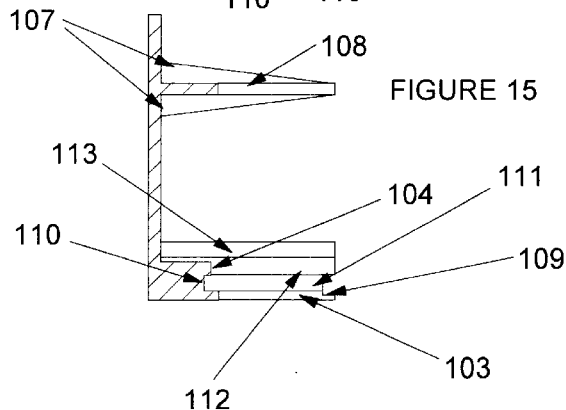
FIGURE 15
FIGURE 16
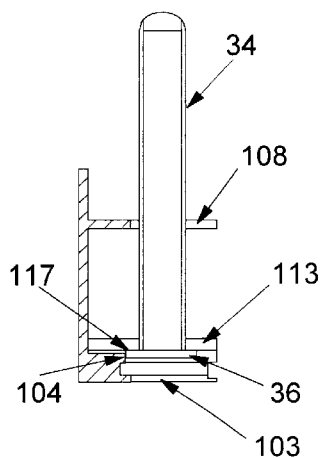
FIGURE 17
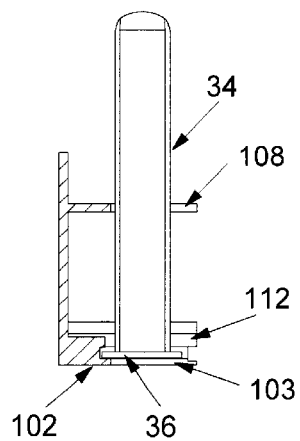
FIGURE 18
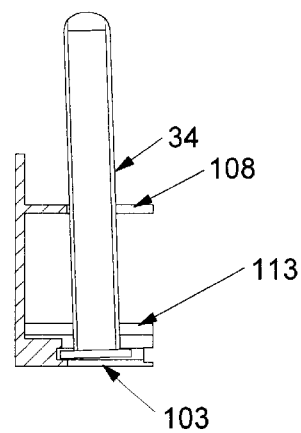

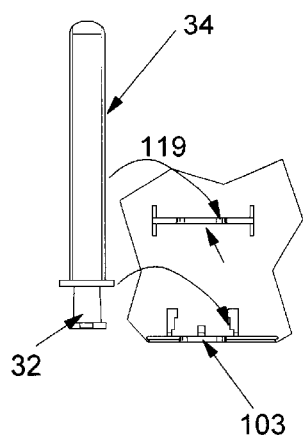
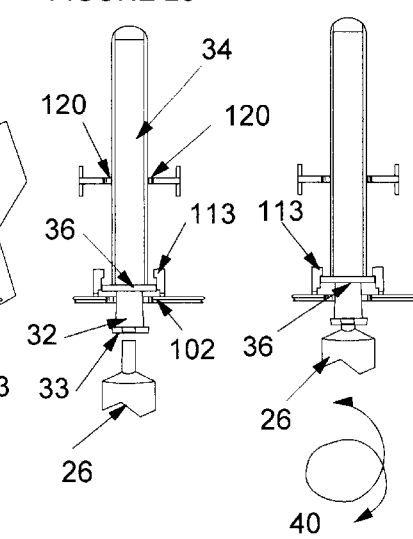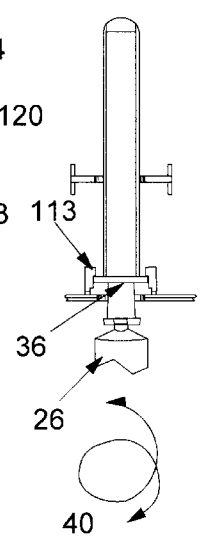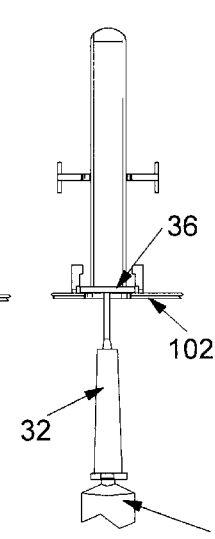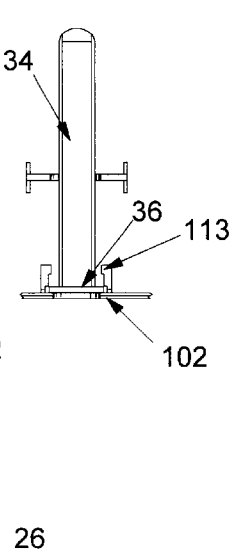
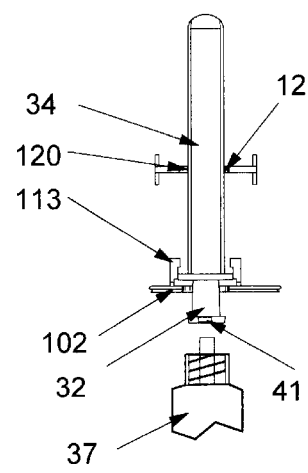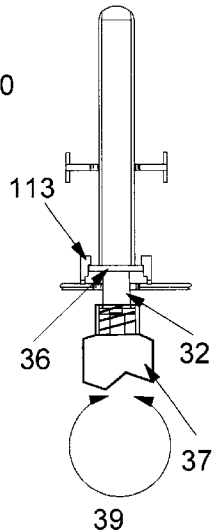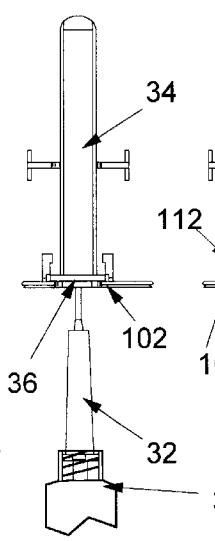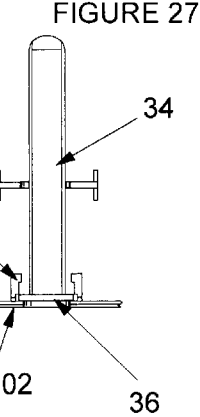

NEEDLE SHEATHING AND UNSHEATHING SAFETY DEVICE

This application is a continuation in part of U.S. patent application Ser. No. 09/453,737 filed Dec. 2, 1999 U.S. Pat. No. 6,257,408.

BACKGROUND OF THE INVENTION

The present invention relates to devices and methods for removing, retaining and replacing hypodermic needle in its cap in a one handed action.

U.S. Pat. Nos. 3,727,749, 4,383,615, 5,311,985, and 5,469,964 are all directed to devices that use substantial friction contact with a needle cap to hold the cap in place while the user attaches to a syringe the hypodermic needle held in the needle cap and thereafter withdraw the needle from the cap.

U.S. Pat. No. 4,846,803 describes a hypodermic needle-cap handling device with a thin rigid plate having an open ended slot therein and a cap holder mounted on one side of plate adjacent the slot for holding a needle cap. A syringe can be manipulated to move a nose thereof into the slot and when the syringe is thereafter moved laterally away from the plate the needle cap, which cannot pass through the slot, is left on the cap holder. The cap can be reapplied to the needle by reversing this action. The cap holder includes an end abutment against which the cap can be urged when the cap is reapplied and spring clips for positively holding a cap on the cap holder. Guide members guide the nose of the hypodermic syringe into the slot and a clamp clamps the hypodermic needle-cap handling device to a table. The device of this patent presents several difficulties. It is intended that the needle cap be braced under spring pressure from the closed end of the needle cap of against resilient material with the open end of the needle cap braced at its edges against the thin rigid plate. The skilled person is frightened at this prospect. It increases the hazard of flying release of the needle cap and its potentially fluid covered needle if the user inadvertently lifts a fraction of a second before the needle hub is truly friction set in the needle cap, if the user tilts the needle cap out of its bracing at insertion of the syringe nose piece, if the thin plate is slippery or if a mistake in manufacture permits other release. Thus, the device of this patent requires an extensive friction grasping device about the barrel of the needle cap to help reduce such risks, although such risks are not eliminated by any means.

As used herein, a hypodermic needle has a sharpened tubular metal shaft mounted to a hub, usually of a polymer, the top rim of the hub extending outward from body of the hub by a small amount (usually as a ring of about one millimeter) and sometimes having further one or more lateral extensions from the rim for thread engagement with Luer-lock syringes. Almost all needle caps by all major manufacturers nearly all have a rim as seen in U.S. Pat. No. 4,846,803, but more important, the needle hub extends a significant length beyond the needle cap rim when the hub is inserted to form a friction fit in the needle cap.

SUMMARY OF THE INVENTION

The present improvement over the rail type embodiment described below is a device and method for removing a hypodermic needle from, storing and replacing the needle in a needle cap. The needle cap rim is captured between a front wall and abutment means behind it. This is done by making aligned slots in the front wall and abutment means with side to side widths greater than the diameter of the needle cap body (without ridges) but less than the outside diameter of the needle cap rim. However, the rim of the needle hub is located outside the front wall slot, where the intervening needle hub rim to needle shaft part of the needle hub passes through the front wall slot and into the needle cap for friction fit contact. A rotation preventing slot is formed in at least a short wall section on the non-front wall side of the abutment means and is aligned with the other slots. The rotation preventing slot supports the needle cap toward the closed end of the cap while the captured rim of the needle cap securely supports a horizontal position. The rotation preventing slot has a smaller side to side width than the width of a needle cap at the ridges on opposite longitudinal sides of the cap but larger than the diameter of the needle cap body without ridges. Thus, rotation of the needle hub to connect or disconnect it to a syringe doesn't cause the needle cap to rotate.

The objects of the invention are to provide a needle sheathing safety device that securely holds the cap of a hypodermic needle, thereby reducing the users risk of being inadvertently pricked when sheathing and unsheathing the needle, to provide a needle sheathing safety device that securely holds the needle of a hypodermic needle, thereby reducing the users risk of being inadvertently pricked when sheathing and unsheathing the needle, to provide a needle sheathing safety device that is easily manufactured and operated, and to provide a needle sheathing safety device that retains the needle in a secure location for convenient and safe resheathing.

In a rail type embodiment, this invention results from the realization that an easier to use and therefore safer needle sheathing safety device is effectuated by a needle sheathing safety device having a plurality of spaced openings for grasping and securely holding a hypodermic needle and cap. This embodiment features a container body housing; a plurality of spaced apart and axially aligned openings for grasping and securely holding a needle cap and needle in the body housing. In most embodiments, the body housing is configured to position the users hands free and clear of the needle during the sheathing and unsheathing operation. Additionally, the plurality of axially aligned openings preferably has means for securely retaining the needle cap needle in the device. In another rail type embodiment, the needle sheathing safety device has a multiple of plurality of axially aligned openings for accommodating the sheathing, unsheathing and retaining multiple needles. In most embodiments the axially aligned openings are U shaped to better accept the portion of the hypodermic needle disposed therein. Of course, the openings may take on other shapes as well, such as squared corners. The plurality of axially aligned openings generally comprises an opening located at an end of the body housing and a second of the plurality of openings disposed in the body housing yet in relative close proximity to the opening located in the end of the body housing. The combined configuration of the opening located in the end of the body housing and the second opening position next there to operate to grasp and retaining the needle and needle cap in the needle sheathing safety device of the present invention. Other openings which are also axially aligned with the end opening are most often disposed in the body housing for grasping and retaining the needle. This invention is preferably constructed of lightweight, needle puncture resistant and inexpensive materials such as hard plastics. The important feature of the materials of construction is that the materials prevent the penetration of the needle, thereby alleviating the risks of inadvertent needle puncture. The body housing is generally configured so that the user need not hold the device in the vicinity of the sheathing and unsheathing process. The invention may also be attached to work surface, thereby obviating the risk that a health care provider prick their free hand with the hypodermic needle.

In an improvement to the rail type embodiment, the rims of the needle cap and the needle hub are separated by a slotted front wall. This lets the user insert and rotate a syringe to attach the needle hub from a position in front of the front wall, withdrawing the needle from the needle cap and leaving the needle cap behind in a secure horizontal position.

BRIEF DESCRIPTION OF THE DRAWINGS

FIGS. 1–7 are the rail type embodiment described above. The remaining figures are for an improvement over the rail type embodiment.

FIG. 1 is a perspective view of the needle sheathing safety device of this invention.

FIG. 2 is a detailed view of the rails comprising the preferred embodiment of the needle sheathing safety device shown in FIG. 1.

FIG. 3 is a view of a hypodermic needle for use in the invention shown in FIG. 1.

FIG. 4 is a detailed view of the needle hub and cap of the hypodermic needle shown in FIG. 3.

FIG. 5b is a side view of the needle cap of FIG. 5a.

FIG. 6 is a top view of the invention of FIG. 1 depicting three needles and needle caps retained in the invention of FIG. 1.

FIG. 7 is a perspective view of the present invention of FIG. 1 showing a needle operably positioned therein.

FIG. 8 are partial side views of four common syringe tips (A, B, C, D) for connection with the hubs of common hypodermic needles.

FIG. 9 is a side view of Luer slip tip syringe connected to a needle, the needle shown still connected with the needle cap.

FIG. 10 is a side view of the Luer slip tip syringe in connection with a needle hub.

FIG. 11 is a side view of a Luer-lock syringe in connection with a needle hub.

FIG. 12 is a front perspective view of the invention device showing part of a front wall and support floor.

FIGS. 13 and 14 are top views of FIG. 12.

FIG. 15 is cross section AA of FIG. 14.

FIGS. 16, 17 and 18 show respectively the device of FIG. 15 with a needle cap in stages of syringe tip insertion to a needle hub (not shown), withdrawal of a needle hub (not shown) from the needle cap, and secure disengagement.

FIGS. 19 and 20 show the steps of placing a needle cap with a needle in the device of FIG. 13.

FIGS. 21–23 respectively show the steps of a slip tip syringe engaging the needle hub of FIG. 20, withdrawing the needle, and a secure disengagement of the needle cap thereafter.

FIGS. 24–27 show the steps of FIGS. 20–23 although for a Luer-lock syringe.

DETAILED DESCRIPTION OF THE INVENTION

The rail type embodiment is now discussed with reference to FIGS. 1–7.

Figure 1:
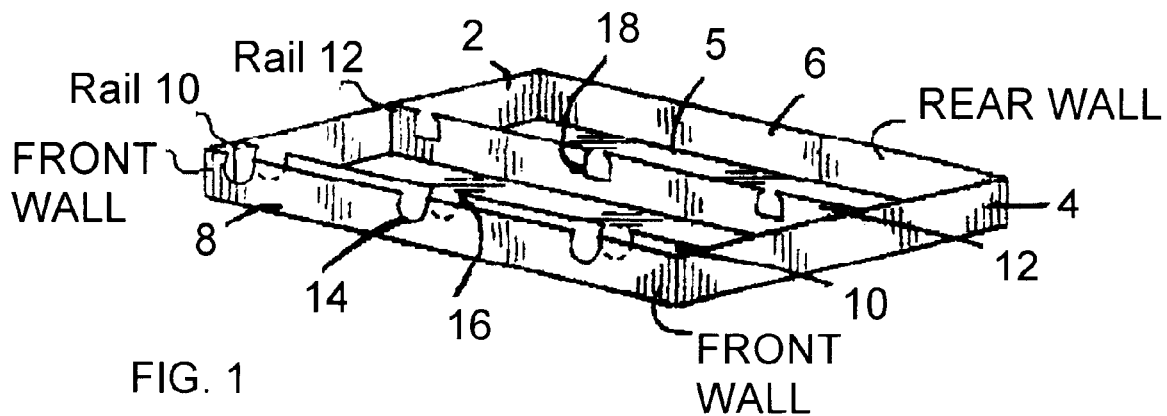
Figure 2:
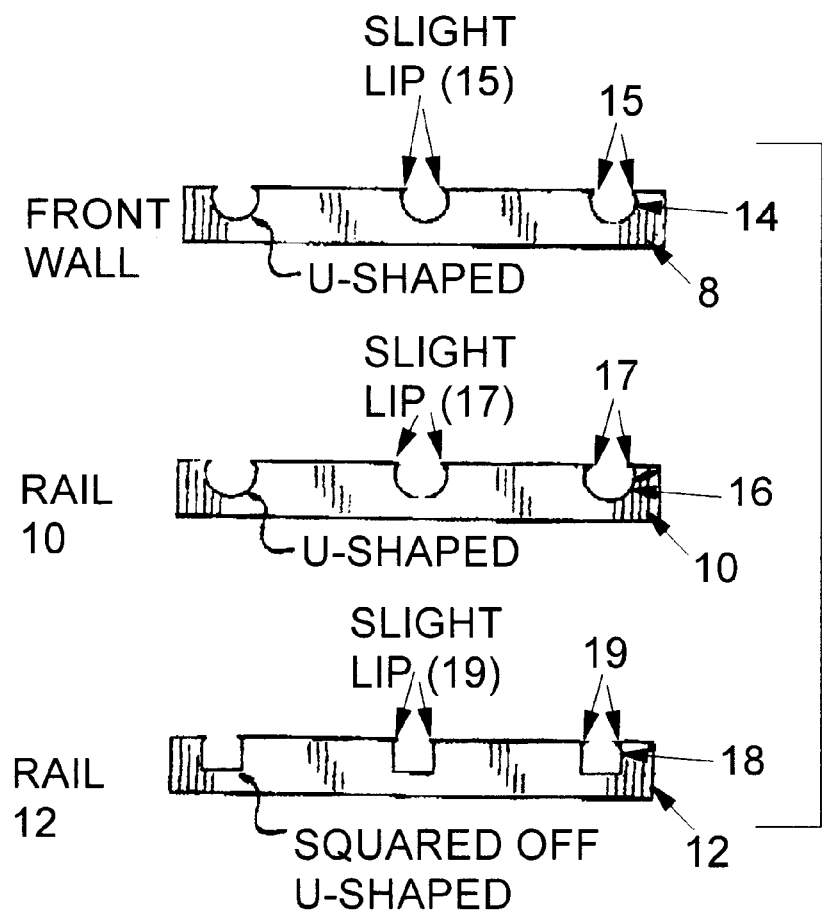
Figure 3:
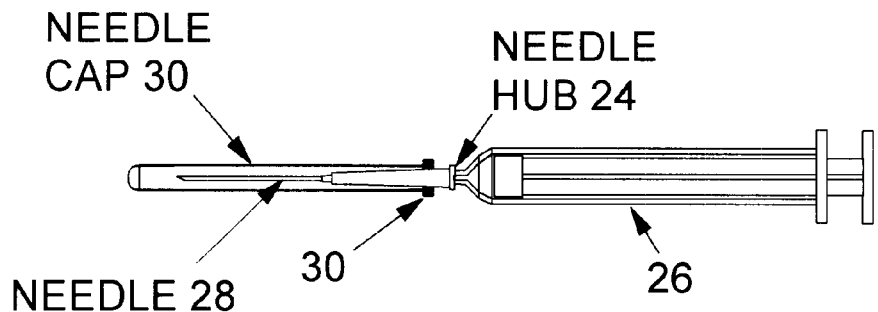
Figure 6:
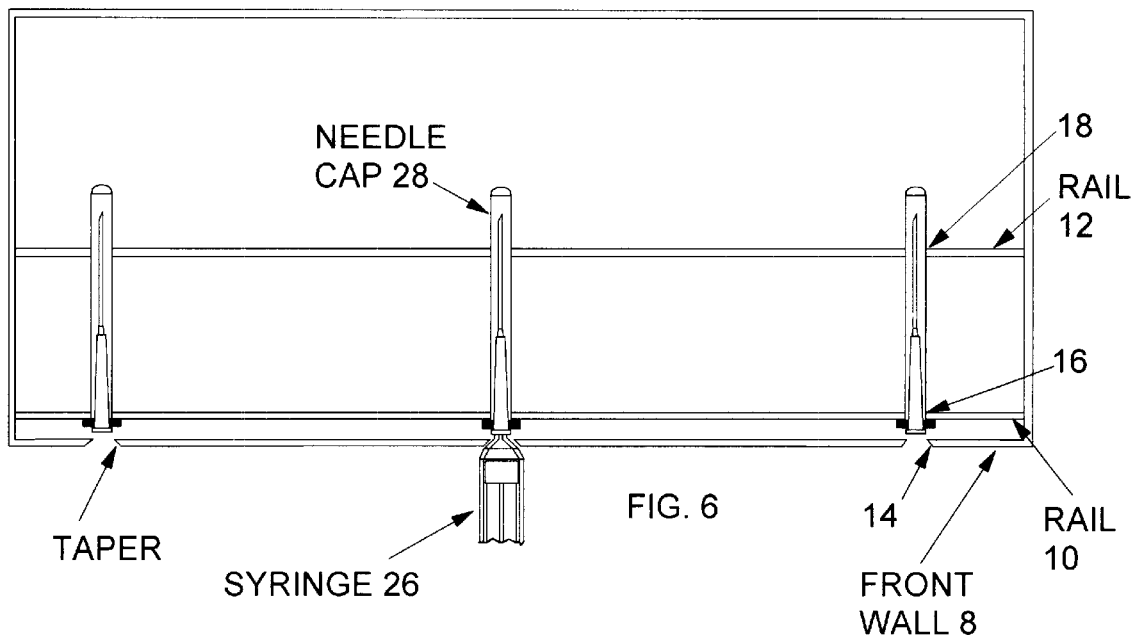
Figure 7:
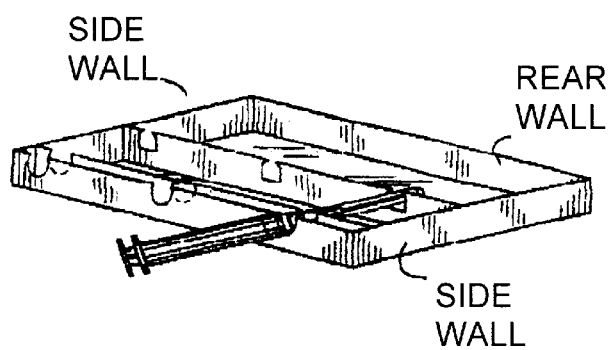

Needle sheathing safety device line, FIG. 1, of the present invention comprises a body housing comprising a front wall 8, a rear wall 6 and side walls 2 and 4 and a bottom 5. In the preferred embodiment sticker depicted, the body housing is substantially rectangular shaped housing containing the other operable structural components of the invention. The front wall 8 has an opening 14, generally U shaped, to facilitate the placement of a needle hub therein. Accordingly, opening 14 is sized to accept a needle cap hub that will be used with the needle sheathing safety device 1. Also located in the body housing of the needle sheathing safety device line is a rail 10 and a rail 12. Located in the rail 10, are openings 16. Also shown are openings 18 disposed in rail 12. The openings 16 disposed in rail 10 and the openings 18 disposed in rail 12 are each axially aligned with each other and with the openings 14 located in front wall 8. In other words, for each opening 14 in the front wall 8, there is a corresponding axially aligned opening 16 in rail 10 and a corresponding axially aligned opening 18 in rail 12. The axially aligned openings in the front wall and spaced apart rails 10 and 12 in combination operate to accommodate a needle cap and needle hub during the process of sheathing and unsheathing of a hypodermic needle as shown in FIGS. 6 and 7. A better understanding of the front wall 8, the rail 10 and the rail 12 may be understood by referring to FIG. 2. The FIG. 2 shows that the front wall 8 and the rail 10 have substantially rounded U shaped or oval openings, 14 and 16 respectively. Although appearing substantially the same size, the openings 14 in front wall 8 actually extend lower than the rail 10 openings 16. The front wall 8 openings 14 extend lower than the rail 10 openings since the needle hub 24, FIGS. 3 and 4, typically has a greater diameter at the point of contact with the front wall 8 then at the point of contact with rail 10. Although this is the preferred embodiment, the front wall 8 openings and the rail 10 openings may be of the same size. The important feature is that the top of openings 14 and openings 16 extend above the needle hub and needle cap respectively of a hypodermic needle fully and operably inserted into the needle sheathing safety device 1.

Figure 4:
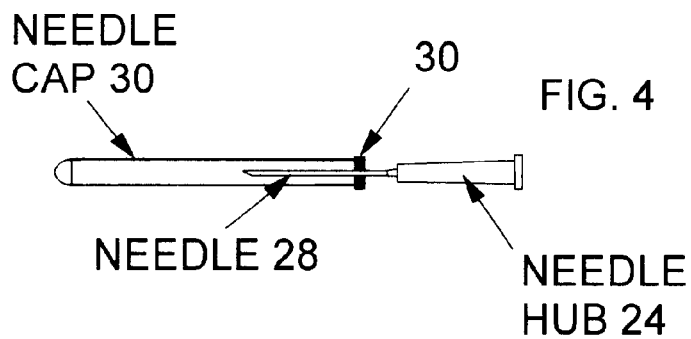
Figure 5A:
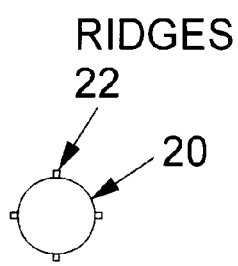
FIG. 5a is a detailed view of a particular type of needle cap used in the invention of FIG. 1.
Figure 5B:
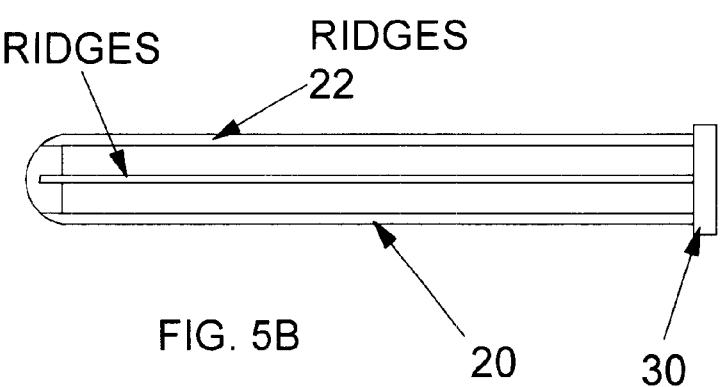

The openings 14, 16 and 18 all have slight lips to grasp and securely retaine the needle cap and needle in the needle sheathing safety device 1. The FIG. 2 shows the lips 15 on the front row 8 openings 14 at the upper inside edge of the openings 14; the lips 17 on rail can openings 16 at the upper inside edge of the openings 16; and the lips 19 on rail 12 openings 18 at the upper inside edge of openings 18. When the needle cap and needle of a hypodermic needle are inserted into axially aligned openings 14, 16 and 18, the needle 20, FIG. 4, is positioned in the opening 18 of rail 12 with the top of the needle cap below the top of opening 18. Since the lips 19 extends slightly above and over the top of the seated needle 20, the needle 20 is held in the opening 18. The fully seated needle cap 20 will also have lips 17 of the opening 16 slightly extending over the rail can openings 16. Thus, the needle cap flange 30 is prevented from accidentally becoming disengaged from the opening 16. The fully seated needle cap 20 will also be positioned such that the opening 14 lips 15 extends slightly over the needle hub 24, thereby securely retaining the needle hub 24 in the needle sheathing safety device 1 until removed by the user.

The front wall 8 and the rail 10 are in relatively close proximity to each other since the needle cap flange 30 is typically relatively thin and the front wall 8 opening 14 grasps the needle hub 30 and the rail 10 opening 16 grasps the needle cap just beyond the needle cap flange 30. In the preferred embodiment, the front wall 8 openings 14 exterior side faces are chamfered, that is beveled, so that the needle hub 24 may be easily seated down into the opening 14 and so that the initial unsheathing of the needle 20 is done gradually without the need for the user to exert undue force. The beveled exterior face of the openings 14 also eases the resheathing process since the syringe 26 may be brought slightly closer to the needle hub 24, close enough to frictionally lock the needle hub 24 onto the needle cap 30 prior to the user lifting and removing the hypodermic needle from the needle sheathing device 1. Constructing the body housing of this needle sheathing safety device 1, at least the front wall 8, of resilient materials that give slightly under nominal force from the user also facilitates and eases the resheathing process.

In most embodiments, including the preferred embodiment, the rail 12 openings 18 have squared bottoms. The openings 18 squared off bottoms are particularly designed to present Luer-lock type needle caps, FIGS. 5a and 5b, from rotating. This is important when sheathing and then reshearthing Luer-lock needles since these types of needles are threadedly attached to syringe 26 of hypodermic needle. The squared off bottoms of openings 18 prevent the needles 20 from rotating by impeding the rotation of the needle cap ridges 22 as syringe 26 is rotated in an effort to remove or attach the needle from or to the syringe 26. Since the needle 20 and the needle hub are in frictional contact, the needle 28 is also prevented from rotating. The user may load and unload Luer-lock needles simply by inserting the needle 20 in an opening 18 and then screwing or unscrewing syringe 26 from the threadedly attached needle hub 24. While the squared off bottoms of opening 18 are particularly useful in the instance of working with threaded type needles, the squared off bottoms can adequately accommodate friction fit needles and needle caps without ridges.

Within the scope of this invention are means for attaching the needle sheathing device 1 of the present invention to a work surface so that the user need not hold the device in their hand. This too reduces the risks of a user becoming accidentally pricked by a contaminated needle. A variety of attachment means are contemplated and covered by this invention as understood by those skilled in the art, including but not limited to adhesive tapes, temporary adhesives, hook and loop fasteners and mechanical means.

Improvement Embodiment

The present invention captures the rim of the needle cap behind a front wall with the needle hub rim on a front side of the front wall. The needle hub passes through a front wall slot that keeps the rim of the needle cap from passing through it when the needle is removed from the cap by attachment to a syringe.

FIGS. 8–11 are depictions of current widely used syringe tips and their operation with common hypodermic needles and needle caps. FIG. 8 shows tips A–D, where tip A is a common Luer-lock syringe and tip B is a Luer slip tip. A Luer slip tip requires that the user press the tip in a spiral motion 40, as in FIG. 10, past rim 33 and into needle hub 32 to form a friction fit connection with the inside surface of the needle hub 32. Even an relatively inexperienced user is capable of this action. However, a more secure connection is made with the Luer-lock syringe of FIG. 11, where clockwise rotation connects syringe 37 with hub 32 by threaded connection with lateral extension 41 from rim 33. Removal of the hub 32 from syringe 37 is done by counterclockwise rotation of the hub 32 into the cap 34. Cap 34 has ridges 35 and rim 36. It can be appreciated from FIG. 9 that substantial, although predictable, length of hub 32 is left exposed between rims 33 and 36 at the pre-removal stage from the cap 34.

Figure 29:
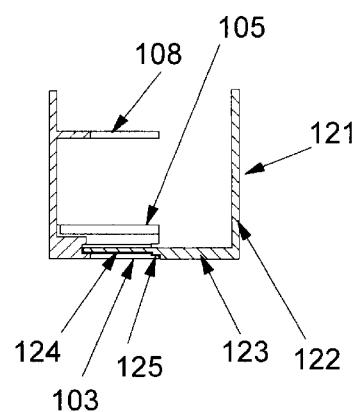
FIG. 29 shows a cutaway side view of the sharps box embodiment of the invention, where the front wall is integral with a sharps box, the top part of which is provided with a closure plate for the front wall slot.
Figure 30:
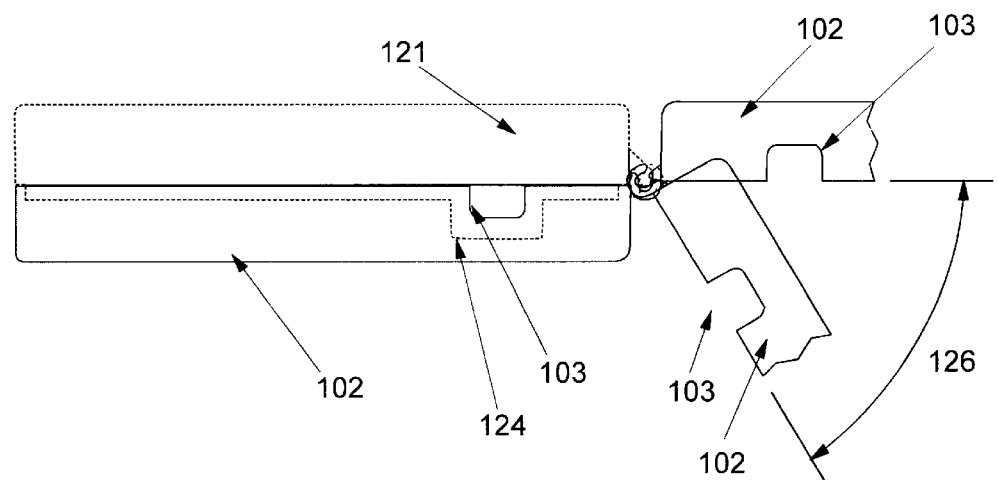
FIG. 30 is a side view of a generalized sharps box with a closure plate for a U shaped slot as in the invention for FIG. 29.

The invention device 100 of FIG. 12 shows a broken away floor 101 having an edge with an upwardly extending front wall 102. The floor 101 side of front wall 102 is the inside of that wall. On the inside are abutment means 105 and rotation preventing means. These means have a wall section 106 supported with extensions 107 and having a rotation preventing slot 108 adapted to prevent rotation of needle caps as in the previous rail type embodiments. A bottom rest support 104 is shown through the front wall slot 103. The device 100 is adapted to rest on a substantially horizontal surface. The device is especially well adapted to integration in to a sharps container as used in surgical procedures, as shown in FIGS. 29 and 30, discussed below. The slots formed by the front wall 102, abutment means 105 and wall 106 are aligned to accept a needle and needle cap 34 combination shown in FIGS. 10 and 11.

The top view in FIG. 13 of the invention device 100 shows the relationship of the slots, walls and abutment means. The abutment means 105 comprise two opposing posts with vertical and directly opposing "steps" 111–113 effectively forming one or more slots each with a side to side width. The "riser" surface between the steps is where the needle cap rim will be stopped from being pushed toward wall 106 in the syringe connection stage of the invention. Steps 113 have side to side width less than that of the outside diameter of rim 36 of cap 34 in FIG. 10. However, that side to side width is just greater than the non-ridge outside diameter of cap 34, allowing the rim 36 of cap 34 to be supported on support 104 while the other end of cap 34 is supported in slot 108 in wall 106. Support 104 is stepped in at support 110 to the same thickness as step 111. In an effective commercially acceptable embodiment, step 112 is about 2 millimeters and step 111 is about 1.5 millimeters, while the height of the posts, front wall 102 and wall 106 is about 15 millimeters, slots 103 and 108 are about 6 millimeters across and 8 millimeters high, while the side to side width between steps 112 and 111 is about 7 and 8 millimeters respectively. The difference in side to side widths of steps 111 and 112 is to accommodate more than one diameter rim 36 of a cap 34.

The cross section AA of FIG. 15 shows that front wall 102 is adapted to have a detent rim 109 which is of use in the integration of the invention into a sharps box as shown in FIGS. 29 and 30.

The cap 34 of FIG. 10 is shown in the remaining figures rotated 90 degrees so that the four ridges 35 are shown at the outer edges at an oblique angle to their radial extension from the barrel of the cap 34. This is the rotation prevention orientation contemplated by the rail type embodiment with the several forms of the rear rail openings to rotationally preventively receive the cap 34. FIGS. 16–18 show such a cap 34 engaged in the invention device, especially in connection with slot 108 (substantially equivalent in function and design with the rail 12 embodiments of the rail type embodiments).

FIG. 16 shows cap 34 in a rear most position with a lower side of rim 36 abutting the vertical edges of the "riser" between steps 113 and 112, forming an abutment interface 117. This is the same position for cap 34 seen in FIGS. 21 and 25 where the cap 34 is pushed away from the front wall in order to obtain a friction fit of a syringe tip to a needle hub 32.

FIG. 17 shows cap 34 in a forward most position where a top of rim 36 abuts the inside surface of front wall 102 around slot 103 and forming an abutment interface 118 as seen in FIGS. 21 and 25 where cap 34 is drawn toward the front wall in the motion of drawing needle hub 32 from cap 34.

FIG. 18 shows cap 34 in a secured and disengaged position after the actions of the FIGS. 16 and 17, with a vertically lower outer edge of rim 36 supportively resting on post 104 and/or section 110 thereof. FIGS. 23 and 27 show that same position from a top view. Cap 34 need not be tightly held in the invention device 100 in this position. The action of gravity on cap 34 keeps it in a condition for easy re-insertion of hub 32 into cap 34 in the reverse actions of those shown in FIGS. 21 and 22 or FIGS. 25 and 26.

FIG. 19 shows how the cap 34 and hub 32 combination are placed in the invention device so that they may be acted upon by the syringes 26 and 37 respectively of FIGS. 20 and 24. In FIG. 19, cap 34 and hub 32 are moved in direction 119 to locate rim 36 effectively within the "riser" distance between steps 113 and 112 and the inside surface of front wall 102 around slot 103, while rim 33 is located outside the front wall 102, hub 32 thereby located as passing through slot 103.

Figure 28:
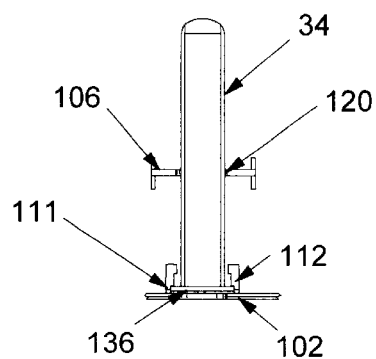
FIG. 28 shows the device of FIG. 12 with a larger diameter needle cap rim accommodated by the dual function abutment means of the invention.

The invention device 100 is adapted to have abutment means that accommodate effective operation on needle caps with one or more substantially different outside diameters of needle cap rims. FIG. 28 shows how a cap 34 with a large diameter rim 36' effectively contacts the abutment means 105 at the "riser" between steps 111 and 112 for the actions that would take place as shown in FIGS. 21 and 25. The actions taken in FIGS. 22 and 26 would equivalently cause rim 36' to contact the inside of front wall 102 around slot 103 to prevent it from sliding through slot 103.

The invention device is particularly effective as an integral piece in a sharps box as shown in FIGS. 29 and 30. Front wall 102 is the peripheral side wall and floor 101 is extended to become the sealed floor thereto of a bottom half of a sharps box, the top half being shown as piece 121. Piece 121 has a floor 122 and side wall 123. Wall 123 has an inside detent rim 125 that sealingly contacts detent rim 109 all around the box to seal in medical sharps inside it. Extending from wall 123 is closure plate 124 adapted to sealingly extend beyond the slot 103 opening for effective retention of medical sharps inside. Plate 124 is adapted to move into and out of sealing position over slot 103 with normal box opening and closing 126.

The above design disclosures present the skilled person with considerable and wide ranges from which to choose appropriate obvious modifications for the above examples. However, the objects of the present invention will still be obtained by the skilled person applying such design disclosures in an appropriate manner.

We claim:

1. A needle sheathing safety device for lodging therein a needle cap, the needle cap comprising a generally cylindrical barrel, with needle cap ribs on an outside surface of the barrel, and a longitudinal bore closed at one end and open at another end, the open bore end defining an opening about which extends a needle cap rim radially from an axis of the bore, the needle cap being adapted to receive into its bore a hypodermic needle, where the hypodermic needle comprises a hollow needle with a longitudinal axis and a needle hub fixed at one end of the hollow needle that extends radially from the needle longitudinal axis to a first radius, where the needle hub is adjacent to a needle hub rim extending radially from the longitudinal axis of the hollow needle to define a second radius, the second radius being substantially greater than the first radius, the improvement comprising:

(a) a floor supporting a substantially vertical sequence of a front wall, abutment means and rear wall;

(b) the front wall defining a first slot with a side to side width less than a diameter of the needle cap rim but greater than diameter of the needle hub;

(c) abutment means near to the front wall and defining one or more second slots, each with a side to side width less than a diameter of the needle cap rim but greater than diameter of a barrel of the needle cap;

(d) a rear wall defining a third slot with a side to side width less than an effective outside diameter of the needle cap ridges but greater than a diameter of the barrel;

(e) having the first, second and third slots aligned and spaced apart such that when the needle hub is secured in the needle cap within a part of the bore near the open end, the needle cap rim is separated from the needle hub rim to define an intervening part of the needle hub, so that the needle cap and hypodermic needle may be placed in the device with the needle hub rim a front side of the front wall, the intervening part is located within the first slot, and the needle cap rim is secured between the first slot and the second slot.

2. The device of claim 1 wherein the abutment means comprise two or more second slots.

3. The device of claim 1 wherein abutment means has an abutment interface surface for the second slot spaced apart from a back side of the front wall around the first slot to define a first distance.

4. The device of claim 3 wherein the first distance is at least a thickness of the needle cap rim.

5. The device of claim 4 wherein the first distance is two or more times the thickness of the needle cap rim.

6. The device of claim 4 wherein the first distance is less than or equal to the intervening part less the width of the front wall.

7. The device of claim 5 wherein a side to side width of a first of the second slots is greater than a side to side width of an adjacent second of the second slots.

8. The device of claim 7 wherein the first of second slots is the second slot closest to the first slot.

9. The device of claim 1 wherein the rear wall is located apart from the second slots by a distance such that the needle cap can rest in a horizontal position supported by a lower post of the abutment means and a bottom of edge of the third slot.

10. A system for using a needle sheathing safety device for lodging therein a needle cap, the needle cap comprising a generally cylindrical barrel, with needle cap ribs on an outside surface of the barrel, and a longitudinal bore closed at one end and open at another end, the open bore end defining an opening about which extends a needle cap rim radially from an axis of the bore, the needle cap being adapted to receive into its bore a hypodermic needle, where the hypodermic needle comprises a hollow needle with a longitudinal axis and a needle hub fixed at one end of the hollow needle that extends radially from the needle longitudinal axis to a first radius, where the needle hub is adjacent to a needle hub rim extending radially from the longitudinal axis of the hollow needle to define a second radius, the second radius being substantially greater than the first radius, the improvement comprising:

(a) a floor supporting a substantially vertical sequence of a front wall, abutment means and rear wall;

(b) the front wall defining a first slot with a side to side width less than a diameter of the needle cap rim but greater than diameter of the needle hub;

(c) abutment means near to the front wall and defining one or more second slots, each with a side to side width less than a diameter of the needle cap rim but greater than diameter of a barrel of the needle cap;

(d) a rear wall defining a third slot with a side to side width less than an effective outside diameter of the needle cap ridges but greater than a diameter of the barre;

(e) a needle hub and needle cap combination, in which when the needle hub is secured in the needle cap within a part of the bore near the open end, the needle cap rim is separated from the needle hub rim to define an intervening part of the needle hub;

(f) having the first, second and third slots aligned and spaced apart such that when the needle hub is secured in the needle cap within a part of the bore near the open end, the needle cap rim is separated from the needle hub rim to define an intervening part of the needle hub, so that the needle cap and hypodermic needle may be placed in the device with the needle hub rim a front side of the front wall, the intervening part is located within the first slot, and the needle cap rim is secured between the first slot and the second slot;

(g) having the first, second and third slots aligned and spaced apart so that the needle cap and hypodermic needle may be placed in the device with the needle hub rim a front side of the front wall, the intervening part is located within the first slot, and the needle cap rim is secured between the first slot and the second slot; and (h) placing the needle hub and needle cap combination in the device such that the needle cap rim is outside the front wall, the needle hub rim is between the first slot and one of the second slots, and the barrel is located in a non-rotatable position in the third slot.

11. The system of claim 10 wherein a syringe tip of a syringe adapted to be connected with the needle hub via its syringe tip is inserted into the needle hub causing the needle cap to pushed toward the third slot.

12. The system of claim 11 wherein a lower part of the second rim abuts the abutment means at an abutment interface surface around a second slot preventing the needle cap from moving further toward the third slot.

13. The system of claim 12 wherein the syringe obtains a connection with the needle hub, the syringe is withdrawn in the direction it was applied to the needle hub, and a top part of the second rim abuts an inside surface of the front wall around the first slot.

* * * * *